(12) United States Patent
Brunelle et al.

(10) Patent No.: US 6,681,417 B2
(45) Date of Patent: Jan. 27, 2004

(54) THERAPEUTIC SHOWER ENCLOSURE

(75) Inventors: Henry Brunelle, Cap Rouge (CA); Stéphane Baron, Charny (CA); Marc Beland, Lévis (CA); Henri Veyrie, Laval des Rapides (CA); Patrick Lemay, Sherbrooke (CA); Stéphane Bilodeau, Fleurimont (CA)

(73) Assignee: Gestion Ultra International Inc., St-Nicolas (CA)

( * ) Notice: Subject to any disclaimer, the term of this patent is extended or adjusted under 35 U.S.C. 154(b) by 0 days.

(21) Appl. No.: 10/173,637

(22) Filed: Jun. 19, 2002

(65) Prior Publication Data

US 2003/0188378 A1 Oct. 9, 2003

(30) Foreign Application Priority Data

Apr. 4, 2002 (CA) .............................................. 2380710

(51) Int. Cl.⁷ .................................................. A47K 3/22
(52) U.S. Cl. ....................... 4/597; 4/525; 4/524; 4/612; 4/614
(58) Field of Search ............................ 4/524, 525, 612, 4/613, 614, 596, 597, 598; 52/264; 607/87; 34/202, 224, 225, 232, 233

(56) References Cited

U.S. PATENT DOCUMENTS

| | | | | |
|---|---|---|---|---|
| 3,007,178 A | * | 11/1961 | Altman et al. ................. | 4/525 |
| 3,285,693 A | * | 11/1966 | Madl, Jr. ....................... | 4/524 |
| 5,099,587 A | * | 3/1992 | Jarosch ......................... | 34/202 |
| 5,293,653 A | * | 3/1994 | Filipponi ....................... | 4/524 |
| 5,987,662 A | * | 11/1999 | Kiyokawa et al. ............. | 4/524 |
| 6,567,999 B1 | * | 5/2003 | Thurner ......................... | 4/612 |
| 6,623,511 B1 | * | 9/2003 | Daffer et al. .................. | 4/524 |

FOREIGN PATENT DOCUMENTS

| | | | |
|---|---|---|---|
| DE | 3400180 A1 | * | 7/1985 |
| DE | 3911679 A1 | * | 10/1990 |
| EP | 0300577 A1 | * | 1/1989 |

* cited by examiner

*Primary Examiner*—Gregory Huson
*Assistant Examiner*—Khoa D Huynh
(74) *Attorney, Agent, or Firm*—Ogilvy Renault; Guy J. Houle (57) ABSTRACT

A therapeutic shower enclosure is comprised of a bottom wall, sidewalls a top wall and a door assembly in the sidewalls for access to the enclosure. An air blower is mounted above the top wall in communication with one or more air return orifices in the top wall. An air distribution channel is in communication with the air blower and at least one air injecting orifice is provided in the top wall and communicates with the enclosure. A heater is provided in the air distribution channel for heating convected air therein to a temperature of up to about 75° C. to provide a stream of hot dry air circulating in the enclosure about a person's body standing therein whereby to cause the person's body to transpire and provide a therapeutic effect of shedding toxins through the skin. In combination with the hot dry air treatment there is available a chromotherapeutic and luminotherapeutic light treatment and an ion and ozone generator to inject ions and ozone in the hot dry air stream.

40 Claims, 6 Drawing Sheets

THERAPEUTIC SHOWER ENCLOSURE

TECHNICAL FIELD

The present invention relates to a therapeutic shower enclosure wherein hot dry air is generated at temperatures in the range up to from about 50° C. to 75° C. and circulated in the enclosure to cause a person to transpire to provide a therapeutic effect to that person's skin causing it to sweat and shed toxins.

BACKGROUND ART

As long as man has been on this earth, he has made use of the elements of nature to treat, cure and appease different ailments.

Throughout history, a multitude of people, including those of Scandinavian countries, North Africa, Turkey and India have relied on various forms of sweating techniques, to promote good health. From as far back as Ancient Rome and Greece, these civilizations used the sweating process as a means to maintaining, and, in many cases, bringing back health and vigor. A great variety of health problems such as chronic pain, respiratory disorders and skin irritations were treated by this process which they considered as essential to life as food, water and air.

The Aztecs and other people of Mexico and Central America also made use of healthful sweating sessions as part of regular therapeutic and medical practices. Still in use today in Mexico is the Temazcal (a native Nahuatl word), temas, for bath, and calli, for house, where in a primitive-looking stone or mud hut steam bach are practiced.

The same beneficial principles still hold true today. The practice of including sweat has so many therapeutic benefits. It can alleviate a large number of symptoms and largely improve one's health. This induced heat reproduces the effects of a high fever (nature's way of ridding the body of infection) by stimulating and increasing the body's normally occurring internal exchanges. It produces effects similar to those caused by strenuous exercise and raises the metabolism, bringing increased circulation to all muscles, organs and tissues. By calling the body's normal defense mechanisms into action, it greatly stimulates the natural healing process. This overheating of the body helps to eliminate toxins at a much faster rate. Thus, with blood circulation increased and sweating increased, the elimination of toxins is maximized. Considered to be the body's third lung, the skin absorbs nutrients but also excretes what it does not need. Excessive sweating, in a controlled and safe environment, will accelerate this process bringing improved health and well-being.

With aging comes a slowing down of the body's normal healing capacities and this is how deterioration sets in. The body does not excrete internal waste, toxins and hyperacidity, also a cause of weakened and deteriorated organs, muscles and tissues, as it should. Bodily functions are slowed and a degradation of all tissues ensues. The oxidation process begins and allows for the development of illness and diminished physical and mental capacities. We have all heard of antioxidant foods and dietary supplements intended to slow down this process but there are also techniques and practices that prevent the oxidation of the body.

The use of preventive measures is key to continued good health. Physical activities such as regular exercise (where sweating occurs) can help to slow down the aging process. Saunas provide a humid heat that offers limited possibilities. The body is not capable of enduring this combination of high temperature and raised humidity levels for very long as the skin pores react to this extreme humidity by closing up, hindering the elimination process. Whereas an environment that would provide a dry heat would rather cause the skin pores to open and release water to fool the skin and eliminate waste freely allowing the user to easily sustain heat exceeding the body's normal temperature by over 50° Fahrenheit, long enough to produce noticeable results. In these conditions, viruses, bacteria and microbes are virtually annihilated or considerably weakened. Furthermore, it has been scientifically proven that 30 to 40 minutes of intense sweating allows for the elimination of acidity and toxins equivalent to 24 hours of normal kidney function.

Primary sweating is the time spent in the sweating environment, in a sitting position, that opens the pores of the skin for the excretion of toxins and is considered the hygienic portion of the session. This session should take place in a calm and peaceful atmosphere. Secondary sweating is the resting period (post-sweating environment) where the user lies in a strategic position covered by different layers of clothing, sheets and blankets to undergo secondary sweating and is considered the therapeutic portion of the session. This enables the body to sweat abundantly at first, then, sweating diminishes gradually slowly easing the body back to its normal temperature. In this second phase, a much greater volume of toxins and waste is eliminated than the sweating that is generated by a bath or sauna.

It is known to use a shower enclosure to convert it for therapeutic use. However, that therapeutic use has been restricted to the generation of steam in the enclosure to provide a steam bath. Example of such prior art can be found in U.S. Pat. Nos. 5,142,713, 5,293,653. In this latter reference the device for producing steam is incorporated in the roof of an existing shower stall whereby to convert it to sauna. The conversion of the roof consists of a compact box shaped roof having a fan for forced air circulation within the shower enclosure and a vaporizer, supplied directly by a water source through a valve, produces the steam. The vaporizer is operated intermittently by a timer which is interlocked by two thermostats. The steam is circulated by a forced air circulation system.

Steam baths have been known as providing limited therapeutic effect for the reason that the steam deposits water particles on the skin of the user person and provides an insulation to the skin from the temperature in the enclosure. The tolerance of a person being subjected to a steam bath is usually limited to about 120° F. This temperature is not sufficiently high to cause the body to create a defensive mechanism by transpiring and thereby provide a therapeutic effect by eliminating toxins quickly.

To do so the internal temperature of the body needs to be increased towards 101° F. to 102° F. At those temperatures virus and bacteria will die and other beneficial effects are obtained when the internal body temperature is raised to those levels. As pointed out above, it is not possible to achieve this with steam saunas due to the fact that the skin is insulated by the humid environment depositing water on the user's skin.

Sauna devices for small enclosures are also known such as described in U.S. Pat. No. 5,987,662 and wherein the heating device is in the form of a radiation panel which is secured adjacent the ceiling of the enclosure. The radiation panel comprises a resistive heating element which radiates heat within the enclosure. A blower also circulates the air within the enclosure. If the enclosure was a shower stall type enclosure then a person standing or seated in the enclosure would receive this radiation heat directly on his head and this would cause the user person adverse effects making it very difficult to resist the heat radiation as it would not be too concentrated and gradually heat the entire body. Accordingly, this type of device would be unsuitable for use in a therapeutic shower enclosure adapted for use by a single user person. Accordingly, a heater device as disclosed in this patent is not recommended.

The advantages of the therapeutic shower enclosure of the present invention are many, and namely to cleanse the skin through dry heat sweating process, to purify nasal passages by clearing mucous membranes, to reduce stress levels and pain by stimulating the production of endorphins (the "feel good" hormones, to increase body heat reproducing the effects of a high fever, warding off viruses and other micro-organisms, and to stimulate the elimination of accumulated toxins or harmful metal such as lead and mercury, chemical products or fungus present in the body.

Regular sweating sessions offer a myriad of health advantages. In addition to relieving aches and pains related to rheumatism, arthritis and other chronic diseases, they can relieve cold and flu symptoms and congestion, alleviate the discomfort and pain of various skin diseases, as well as bring a strengthened immune system to better health in general.

SUMMARY OF INVENTION

It is a feature of the present invention to provide a therapeutic shower enclosure wherein hot dry air is circulated therein to temperatures in the range of up to 50° C. to 75° C., whereby to cause a user person's body to transpire and provide a therapeutic effect of shedding toxins through the skin. Dry heat as opposed to a sauna which is humid will allow for a much higher shower enclosure temperature about 150° F. compared to 110°–120° F. for saunas.

Because it is dry heat, no humidity will cover the skin. Therefore, because it protects itself, the skin will sweat a lot more through perspiration. This will help the metabolism cool down and cleanse the pores eliminating more toxins, oils, sebum . . . .

Because a higher temperature can be tolerated, the transfer of heat from the air to the derm and from the derm to the epidermis will increase the body temperature by 2 to 4° which will create an artificial fever. This fever is the body's way of weakening and killing viruses, bacteria.

Another feature of the present invention is to provide a therapeutic shower enclosure wherein the user's internal body temperature can approach 101° F. to 102° F. wherein to stimulate the immune system of the user to cause it to sweat thereby killing microbes in the user's system which do not resist at those temperatures and wherein the person's system will undergo a disintoxication due to heavy transpiration.

Another feature of the present invention is to provide a therapeutic shower enclosure having a hot air temperature distribution system for circulating hot dry air at temperatures in the range of up to 50° C. to 75° C. in the enclosure and which is used in combination with a chromotherapeutic system comprised of colored lights.

Another feature of the present invention is to provide the therapeutic shower enclosure as above described and also incorporating in combination therewith a luminotherapeutic system which consists of intense clear light being generated in the enclosure.

Another feature of the present invention is to provide a therapeutic shower enclosure as above described and wherein the hot dry air stream is injected with ions which provides negative charges in the air stream to subject the user to an energizing environment.

Another feature of the present invention is to provide a therapeutic shower enclosure as above described and wherein ozone is injected in the hot dry air stream to provide purification and disinfection of the air to destroy bacteria and other impurities.

The therapeutic shower enclosure of the present invention is essentially a modified shower stall wherein in the top wall thereof there is adapted a hot air heating and circulation system capable of heating the air to temperatures in the range of up to about 50° C. to 75° C. In combination with this source of hot dry air, which provides a therapeutic effect to a user person, there is incorporated other devices which can provide to the user chromotherapy, luminotherapy and other therapies by the injection of ions and ozone into the hot dry air stream.

It is known that heat stimulates the immune system of people and is utilized to kill many types of microbes that cannot resist internal body temperatures in the range of 101° F. 102° F. In effect, as a person sweats the hot air penetrates the epidermis and the derm and will cause the body temperature to increase and thus make it sweat to eliminate toxins. When subjecting one's body to hot dry heat many advantages are obtained as mentioned above. For example, it causes an augmentation of the tissue stretchability, provides a reduction or treatment to muscle spasms and cramps and thereby diminishes muscle pains due to the dilation of the blood vessels. Heat also causes the body to sweat and the blood stream to purify itself by eliminating toxins and reducing the acidity and thereby providing improvements to arthritic and rheumatism problems due to the relaxation of the muscles about the articulations. It is also been proven that elevating the internal body temperature above normal causing hyperthermia, provides an improvement to people having depressions. This result is probably due to the augmentation of endorphins, these are the substances that are produced by the organism when subjected to a physical effort.

Chromotherapy which is light therapy is also well known. Light therapy provides physiological and therapeutic benefits thereby increasing the quality of life. Light and colored light have been long used to treat different illnesses. The biochemistry of the human body depends on light. Color also is derived from light and is the source of life and each color has certain psychological properties which are therapeutic. For example, the red color has been known as a source of strength, health and vitality. Because the color red is a stimulant it activates blood circulation and stimulates the liver. The red color is very energizing and is a treatment against anemia as it forms in one's body hemoglobin. Because red light rays provide heat they provide an excellent treatment for congestion, mucous and other illnesses which are aggravated by cold weather.

Luminotherapy consist in emitting intense clear light which repeat the light spectrum and the intensity of the sun to provide therapeutic effects. Light sources using neon or halogen lights having an intensity of at least 8,200 lux per square meters provide such therapeutic effects. In the therapeutic shower enclosure of the present invention we utilize halogen light sources capable of generating 10,000 lux at 24 inches which simulates the light intensity that we obtain on a spring morning at about 8 o'clock. When the body is exposed to intense light a series of chemical reactions and physiological reactions are created. The therapeutic effects obtained from such light sources are numerous and particularly when utilized in combination with a morning shower. The light helps in reducing the production of melatonin (the hormone when one sleeps) and accordingly helps in recovering from the effects of a night sleep.

Ion therapy is also known as providing an energizing effect to the human body. An ion is formed of molecules which are themselves comprised of certain numbers of atoms which have a positive core and negative electrons. To our hot dry air circulation system we add ions to produce a therapeutic effect to the person undergoing treatment in the shower enclosure. The negative charge of the air particles provides an energizing effect while the negative ions also provide benefits against diseases and particularly permits an improvement of physical and intellectual performance.

Ozone therapy provides excellent properties for purification and disinfection and by injecting ozone in the hot dry air stream of our therapeutic shower enclosure the air and water particles therein are treated by destroying bacteria and impurities therein. All of the above therapies are provided in our therapeutic shower enclosure in combination with the hot dry air stream either simultaneously or individually or in groups and for predetermined periods of time.

According to the above features, from a broad aspect, the present invention provides a therapeutic shower enclosure comprising a bottom wall, sidewalls, a top wall and a door assembly in the sidewalls for access to the enclosure. An air distribution channel is in communication with an air blower and one or more air return orifices and at least one air injecting orifice communicating with the enclosure whereby to create a stream of circulating air in said enclosure. Heating means is provided in the air distribution channel for heating air convected therein to temperatures in the range of up to about 50° C. to 75° C. to provide the stream as a stream of hot dry air circulating in the enclosure about a person's body therein whereby to cause the person's body to increase its internal temperature to cause perspiration to thereby provide a therapeutic effect of shedding toxins through the skin.

The air in the enclosure is heated to a temperature which is preferably within the range of from about 31° C. to 40° C. for a predetermined time span.

The shower enclosure of the present invention is provided with a molded top shell which incorporates therein two air distribution channels which communicate with an air return orifice in the top wall and wherein the hot dry air is released in the shower stall in a downward stream adjacent opposed sidewalls of the enclosure and returns upwardly adjacent a rear intersection region 6f the opposed sidewalls so that an air stream flows from the top wall to the bottom wall and then back up to the top wall to subject a user person to a hot dry air therapeutic stream.

The therapeutic shower enclosure of the present invention also incorporates light sources as well as an ozone and ion generator all of which are mounted above the top wall and to provide therapeutic benefits to a user standing in the shower enclosure. An atomizer may also be used to inject a mist in the hot dry air stream to enhance sweating. The enclosure is also provided with one or more standard shower heads.

According to a still further broad aspect of the present invention there is provided a therapeutic shower enclosure which comprises a bottom wall, side walls, a top wall and a door assembly in the side walls for access to the enclosure. One or more chromotherapeutic light sources secured to the enclosure to subject a user person to coloured light. Control means is provided to energize the light source for a desired predetermined period of time to subject a user person to a chromotherapeutic effect.

According to a further broad aspect of the present invention there is provided a therapeutic shower enclosure comprising a bottom wall, sidewalls, a top wall and a door assembly in said sidewalls for access to said enclosure, one or more intense clear light source in one of said top wall or sidewalls having an intensity of at least 2000 lux, control means to energize said light source for a desired predetermined period of time to subject a user person to a luminotherapeutic effect, said enclosure having a shower head and water control valves.

BRIEF DESCRIPTION OF DRAWINGS

A preferred embodiments of the present invention will now be described with reference to the accompanying drawings in which.

DESCRIPTION OF PREFERRED EMBODIMENTS

Figure 1:
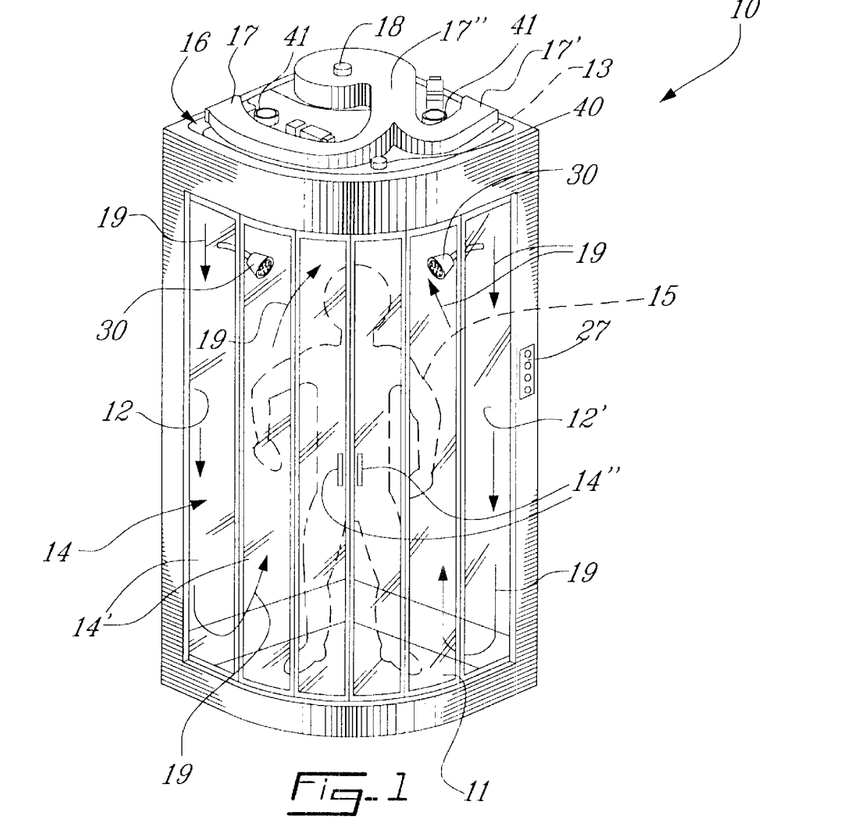
FIG. 1 is a perspective view showing the therapeutic shower enclosure of the present invention with a molded shell mounted on the top wall thereof and incorporating therein a hot dry air system as well as other therapeutic devices whereby to subject a person standing in the enclosure to therapeutic treatments.

Referring now to the drawings and more specifically to FIG. 1, there is shown generally at 10 the therapeutic shower enclosure of the present invention. The enclosure comprises a bottom wall 11, sidewalls 12 and 12', a top wall 13 and a door assembly 14 permitting access to a user person 15 to the enclosure.

Figure 2:
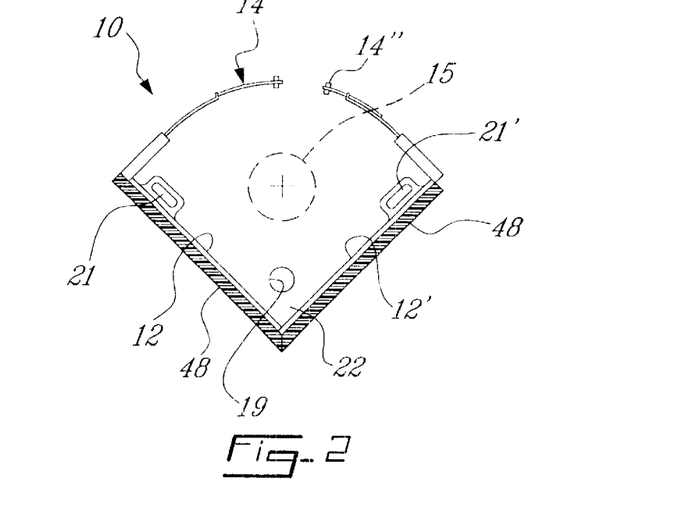
FIG. 2 is a plan view of the inner surface of the top wall of the therapeutic shower enclosure of FIG. 1.

A molded shell 16 is secured over the top wall 13 of the enclosure and has molded therein distribution channels 17 which are in communication with an air blower 18 whereby an air stream 19 is convected downwardly in the enclosure against the sidewalls 12 and 12' thereof and returned through an air return orifice 19 in the top wall 13, as shown in FIG. 2, whereby the user person 15 is subjected to a hot dry air stream to undergo therapeutic effects as will be described hereinbelow.

There are no scientific studies relating to the therapeutic effects by exposing a person's body in a therapeutic shower enclosure or sauna of the type as herein disclosed. However, referring to FIG. 10, scientific studies exist to determine the level of comfort, discomfort or thermal stress caused by extreme heat according to ASHRAE. These known studies relate to the amount of work a person can perform under certain hot environmental conditions whereby people do not produce excessive work under these conditions that could lead to thermal stress, that is to say heat stroke. The known studies of comfort are to determine a neutral point in function with physical parameters of the environment including temperature, humidity radiation and the speed of the air in the environment of the working person. Reference numeral 20 in the enclosed chart depicts the zone in which the therapeutic shower enclosure of the present invention is to function to provide a safe environment to the user. This zone takes into account that the person in the therapeutic shower enclosure is naked as opposed to the parameters of the charts, which were constructed in relation to a person which is likely clothed. The zone 20 is an ideal zone to obtain the therapeutic effects but it goes without saying that a person could develop tolerance to exceed this zone for short periods of time without armful effect.

In a sauna a person is exposed to temperatures that can rise to between 50° C. to 85° C. (ASHRAE). The heat which is felt by the person comes from the radiation from the stones which have been preheated and the heat radiation that is accumulated in the interior surfaces of the wood, usually cedar. In order to balance the high radiant heat, the body will sweat to evaporate water and cool itself. In a sauna care is taken to maintain the humidity relatively low, about 20%, in order to enhance the sweating. The more the humidity is high, the less the body will sweat because the water at the surface of the skin will block the pores, as previously described. There is very little air movement in the air in the vicinity where a person is sitting in a sauna and the air speed is usually estimated between 0.05 to 0.20 m/s. At maximum temperature in a sauna there could be a lack of humidity but it is possible to add water on the stones in order to increase the level of humidity. If we add too much water the sauna becomes uncomfortable and does not permit the body to evaporate sweat which contains water and fat. Accordingly, there is very little control over the air and temperature in saunas.

Depending on the time in which a person is exposed to thermal conditions of hot dry heat, the following therapeutic effects can be achieved. The skin is cleansed by sweating when subjected to dry hot air. The sinus can be unblocked at the level of the nose canals. One can also lose fat by sweating and augmenting the heart rate during the sweating effort. It is also known that when subjecting a body to hot dry heat that it has an effect in reducing stress as endorphins are secreted from the brain by the body to counteract pain such as when one is subjected to a fracture. The increase of the internal body temperature also creates a fever that prevents the effect of virus or microorganisms that one breathes in the air. Another beneficial effect is the elimination of toxins accumulated in the body particularly to people exposed to heavy metals in a working environment, or lead, mercury, B.P.C.s or polychlorinated biphenyl as well as mycotoxins which are produced by mushrooms.

Figure 10:
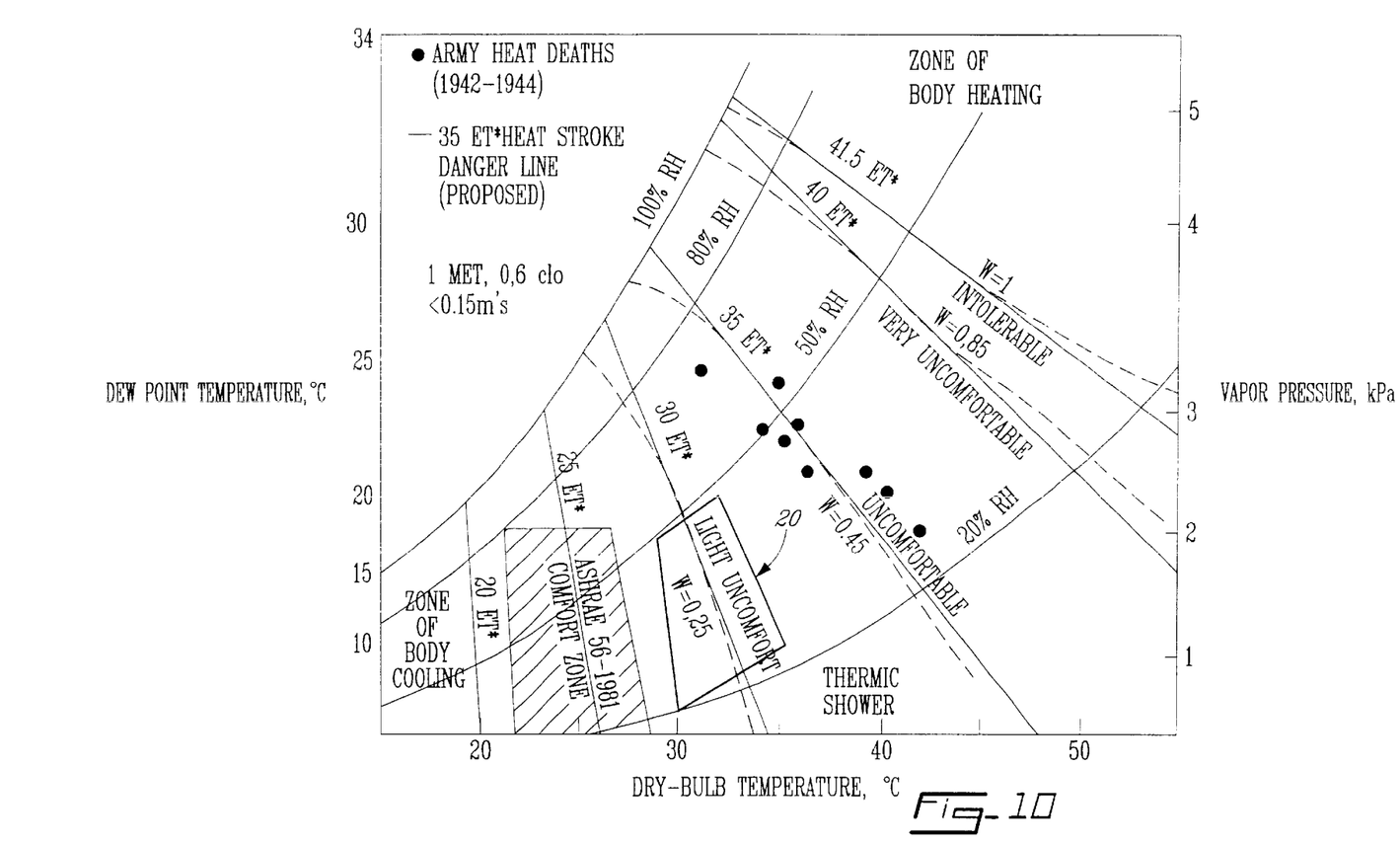
FIG. 10 is a chart showing the effects of heat, dew point temperature and vapor pressure subjected to a human body and identifying the area of operation of the therapeutic shower enclosure of the present invention in said chart.

As demonstrated by FIG. 10 the ideal zone for therapeutic treatment is situated between 31° C. and about 35° C. for people exposed to such hot dry heat for approximately 20 minutes of which there is included a 5 minute period of preheating. It is in this zone that we obtain therapeutic effects and the physiological reaction to heat. For people who have exercised they will appreciate a range which is more elevated, for example 35° C. to 40° C. Also after a person is acclimatized to the therapeutic shower enclosure they can gradually augment the temperature range. It is pointed out that the displacement of air in the enclosure should be approximately 40% and the speed of the air on the user person's body should not exceed about 0.2 m/s.

It has been determined by studies that for temperatures of 38° C. and one hour of exposure, a person can develop a heat stroke. At 46° C. the temperature of the skin will be high enough to start exposing burn rashes. The more tolerant persons can exceed 50 minutes at 52° C. In a sauna one can attain temperature as high as 85° C. but a person should not be subjected to these for long periods of time and it is recommended that the period should be between 5 to 15 minutes maximum.

With additional reference now to FIGS. 2–6 it can be seen that the therapeutic shower enclosure 10 of the present invention includes two slotted injecting orifices 21 and 21' which are in communication with the air distribution channel 17 and 17', respectively, formed in the top wall 13 of the molded shell 16. From experimentation it has been found that these orifices should be slotted orifices having a predetermined dimension to produce a desired air speed in the enclosure. The smaller is the opening the higher is the air speed and the higher is also the static pressure. However, the relationship between the return orifice 19 and the injecting orifices 21 and 21' for a 50 cfm output of the air blower is important in order not to produce excessive noise. From experimentation it has been found that the return orifice 19 should have a diameter of about 3 inches and the air injecting orifices 21 and 21' should preferably be slots of 6 inches by ¾ inch. This relationship of the size of the return orifice to the slot orifices is illustrated in the chart FIG. 13. Experimentation has also been effected as to the location of the return orifice 19 and the chart illustrated by FIG. 12 depicts that ideally the return orifice should be disposed in the corner of the shower enclosure 10, constructed as shown in FIG. 2.

Figure 3:
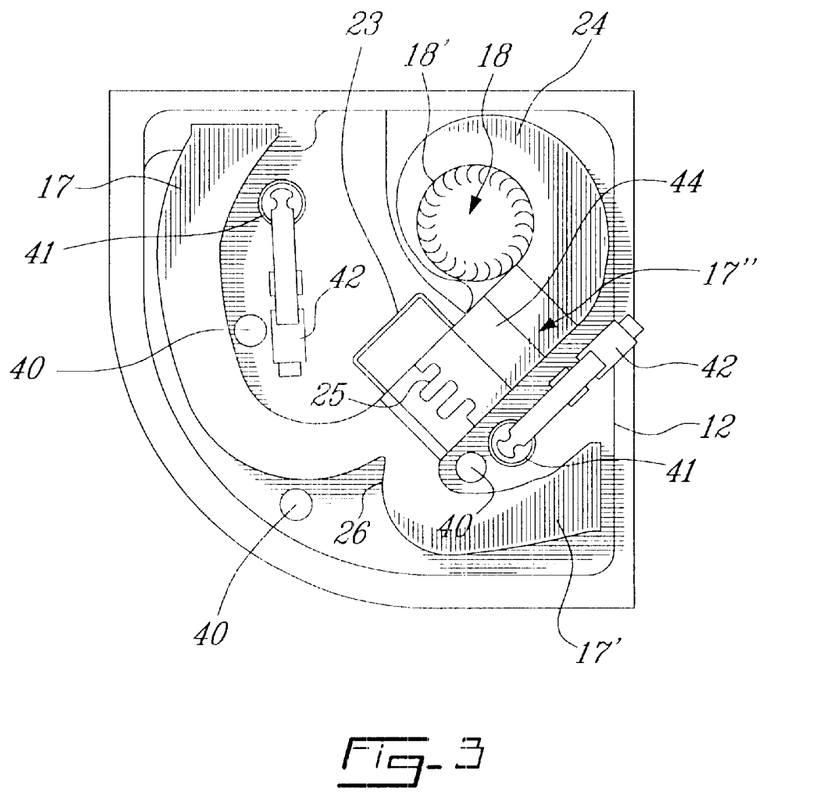
FIG. 3 is a top view of the top wall of the therapeutic shower enclosure of FIG. 1.

As shown in FIGS. 2 and 3 the enclosure is defined by opposed sidewalls 12 and 12' which are disposed at predetermined angles to one another, herein at right angles whereby to define a right angle corner area 22 in the enclosure. The air return orifice 19 is disposed in the top wall in this corner area whereas the air injecting orifices 21 and 21' are disposed spaced adjacent the sidewalls 12 and 12' forwardly of the enclosure whereby a downward air stream, as depicted by arrows 19, is created along the sidewalls 12 and 12' by the injecting orifices 21 and 21' down to the floor 12 and then up returning against the user person 15 to exit through the return orifice 19 along the corner area. As previously described the elongated slot orifices 21 and 21' are dimensioned to provide an accelerated downward air stream adjacent the sidewalls at a pressure which is sufficient for the air stream to reach the bottom wall 11 and to create an air stream comfortable at the head of the user person 15 who is usually standing centrally in the enclosure, as depicted by reference numeral 15 in FIG. 2.

As shown in FIG. 3 an electric heater 23 is secured within the main passageway of the channel in a straight portion thereof to heat the air. The channel also has a convoluted shape 24 surrounding the air blower 18 whereby to produce an accelerated air stream through the heating elements 25, herein resistive heating elements, disposed within the channel and exposed to the air stream created therein by the blower 18. This heater is a 2 kW electric heater. Accordingly, hot dry air is produced in the air stream, and as previously described reaches its set temperature in a time delay of approximately 5 minutes depending on the temperature setting of the control 27. The outlet of the heater 23 directs the hot stream against a forked section 26 of the channel to split the air stream into the two channel sections 17 and 17' associated with the air injecting orifices 21 and 21'.

It is pointed out that although a single return orifice 19 has been shown in the embodiment described herein it is conceivable that more than one return orifice could be provided but they would be of different sizes whereby the system would be balanced.

The heater 23 is capable of heating the air convected therethrough to a temperature of up to about 50° C. to 65° C. to provide a stream of hot dry air circulating in the enclosure about a person's body standing therein. This hot stream of air will cause the person to transpire and provide a therapeutic effect of shedding toxins through the skin. However, the control 27 is provided to select the desired temperature and time of operation (treatment time) by controlling the fan and heater devices. This control 27 can be conveniently and preferably located outside of the enclosure or on the inside wall for ready access to the user person 15. As above pointed out a user person would start using the therapeutic shower enclosure at lower temperatures and progressively increase the temperature and time of exposure depending on his tolerance thereto. However, the ideal temperature is preferably within the range of from about 31° C. to 40° C. and for a predetermined time span of about 20 minutes, this including a time delay of about 5 minutes from start up for the temperature to reach its set value and this for a shower enclosure of about 62 cubic feet and with a blower having a displacement capacity of 65 cfm to maintain air displacement on the user's skin below 0.2 m/s.

As shown in FIG. 1 the shower enclosure is also provided with the conventional showerheads 30 and control valves 30' whereby the user person can use the enclosure as a standard shower enclosure. On the other hand, the showerheads can be activated after a therapeutic bath or even during the therapeutic bath to subject one's body to a cooling shower spray. However, in order to prevent water from being aspired by the blower 18 when the shower heads are operated, a water deflector cover 31 is secured forwardly of the air return orifice 19 to prevent the impeller blades 18' from sucking-in water into the air distribution channels and onto the resistive heating element which would produce excessive steam.

Figure 5:
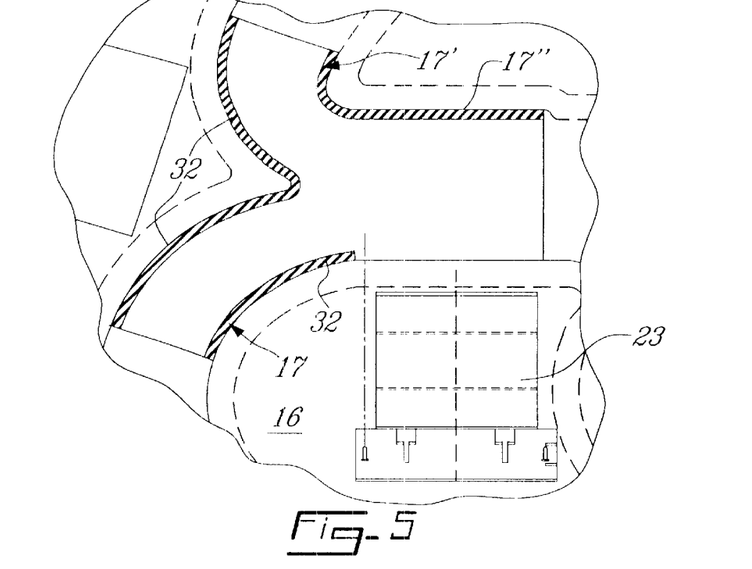
FIG. 5 is a fragmented view showing a portion of the air distribution ducts and the position of the air heating elements.

As shown in FIG. 5 the distribution channels 17, 17' and 17" are covered with a thermal insulation material 32 to prevent excessive heat loss through the top of the molded shell 16. As shown in FIG. 5 the heater 23 is shown pulled out of the main air distribution channel 17".

Figure 6:
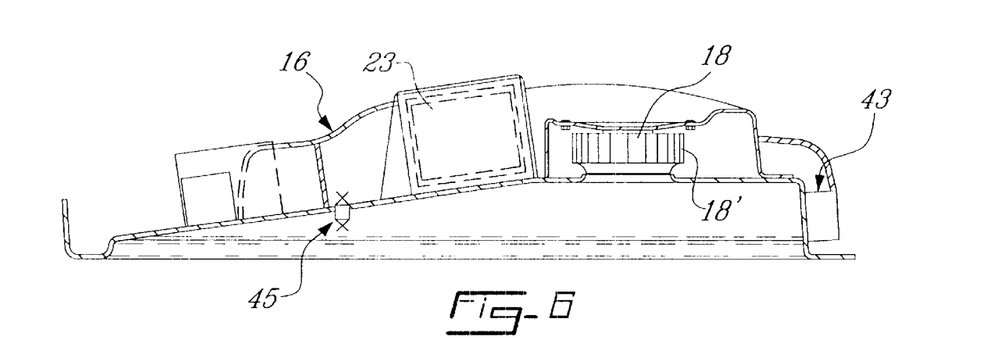
FIG. 6 is a side section view of the shell and partly fragmented.
Figure 7:
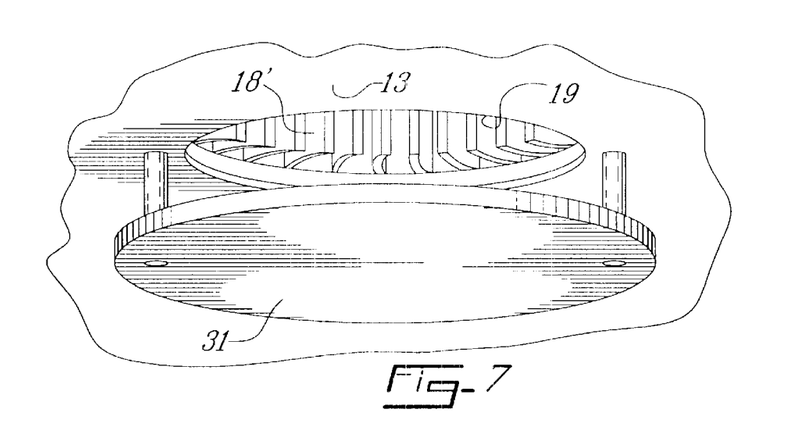
FIG. 7 is a perspective view showing one embodiment of the deflector plate disposed adjacent the return orifice.

FIG. 6 is a transverse and fragmented cross section view of the shell 16 showing the disposition of the blower and heater.

Figure 8:
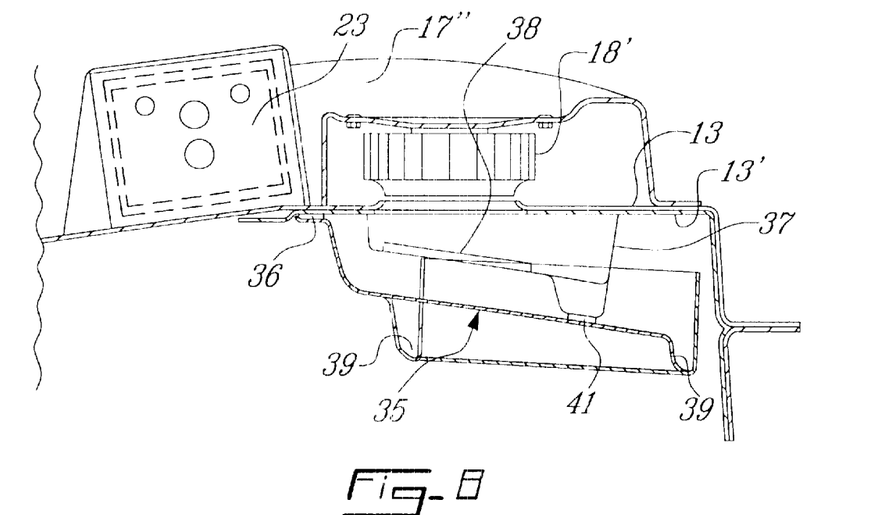
FIG. 8 is a further embodiment showing a further water deflector cover to prevent water infiltration into the return orifice when a shower spray is utilized by the user person in combination with the therapeutic system.
Figure 9:
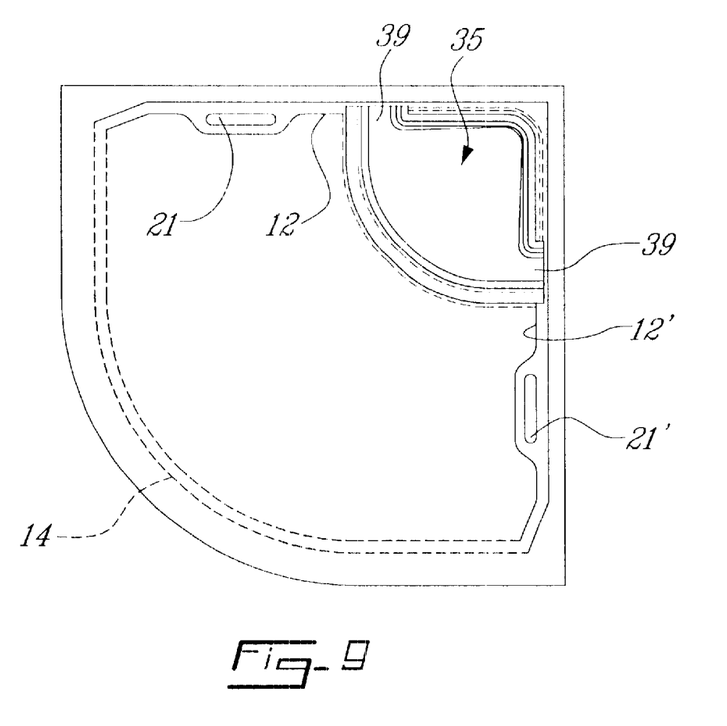
FIG. 9 is a plan view showing the configuration of the deflector and the location of the air injecting orifices.

With reference now to FIGS. 8 and 9 there is shown another embodiment of the construction of a water deflector cover 35 and as hereinshown this cover is connected between the inner face 13' of the top wall 13 by a Velcro™ fastener 36. This cover is necessary to prevent water from the shower heads 30 to be sucked in the air distribution channels or ducts. A filter support frame 37 is also formed with the cover 13 or attached thereto and supports an air filter 38. The deflector cover 35 is provided with convection throughs 39 for accumulating water and/or condensation at the return orifice 19 and directing it against the sidewalls 12 and 12' as better illustrated in FIG. 9. Another Velcro™ fastener 36 interconnects the water deflector cover 35 to the filter support frame 37. Accordingly, the water deflector cover can easily be removed for replacing the filter by simply applying a pulling force thereagainst to detach the Velcro™ fasteners 36 and 40. These Velcro™ fasteners are patches of this material and they constitute detachable attachment means.

Figure 4:
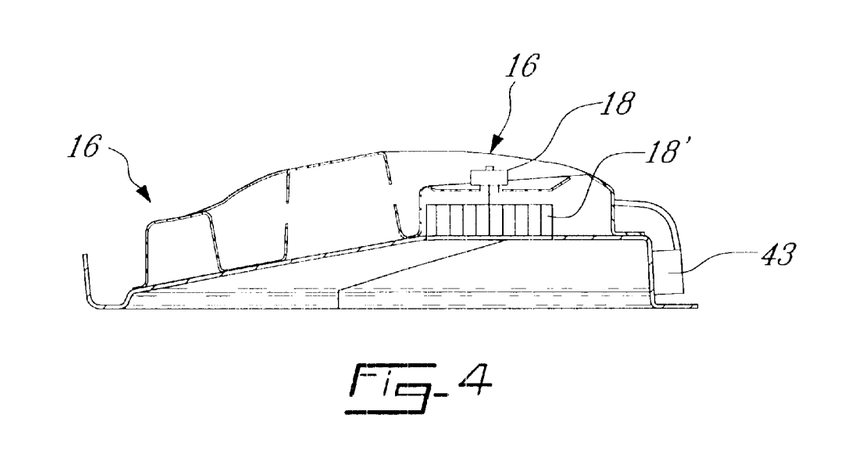
FIG. 4 is a section view of the molded shell which is secured to the top wall of the therapeutic shower enclosure.

With reference now more specifically to FIGS. 3, 4 and 6 it is pointed out that the hot dry air therapeutic shower enclosure of the present invention also includes in combination therewith a chromotherapeutic light source which is provided by at least one colored light source, herein three such light sources 40 being shown and constituted by light emitting diode packs. These lights are controlled by the control panel 27 and a timer circuit, not shown, and they may be actuated through the control panel to have these lights energized for a predetermined period of time whereby the user person may be subject to chromotherapeutic effects. These light emitting diode packs consist of a plurality of light emitting diodes which intensity is modulated by control means (not shown) to produce resultant colors. These light-emitting diodes may be controlled to emit different colors, as selected by a user person or generated automatically, as described in one of my co-pending patent applications, or may be red light emitting diodes. As shown in FIG. 3 these light sources are disposed to the side and forwardly of the enclosure whereby the person's head and vision is exposed to the light source.

The enclosure may also include a luminotherapeutic light sources to subject the user person 15 to intense clear light. This luminotherapeutic light source is also mounted in the top wall 13 and is hereinshown as being constituted by a halogen light source 41, therebeing two of said light sources 41 each fed power by a transformer 42 associated therewith. These light sources are well known in the art. A neon light source would also be a suitable source for generating high intensity light but such would not be practical for use in this application due to their size. These light sources are also actuated by the control 27. The effect of such luminotherapeutic light sources is to bring the intensity of the sunlight in the shower and thus recreate the sunlight's spectrum. This helps the metabolism recognize that it needs to stop producing melatonine (sleeping hormone), and it helps the user person to wake up in the morning. The intensity of the artificial light created by the light sources 41 is 10 000 lux (normal indoor light is between 100 and 500 lux. Regular outside daylight intensity is between 8 200 and 60 000 lux.

The luminotherapy will help to prevent moroseness and winter blues and to sleep better, helps the production of vitamin D which helps absorption of calcium and synchronizes the user person's internal clock by regulating his sleep hormones. This light treatment is particularly beneficial in the wintertime when the light intensity is reduced as the sun is further away from the earth. Daylight is ⅓ of the day (during summer, daylight is ⅔ of the day) which is mostly spent indoors. The suggested therapy time is 20 minutes and it can be used regularly while the user person is taking his daily shower.

The therapeutic shower enclosure is also provided with an ozone generator 43 which is in communication with the air distribution channel 17", at a convenient location between the blower 18 and the heater 23. This ozone generator 43 is a type well known in the art and its purpose is to inject ozone in the hot dry air stream. It is also controlled by the control device 27 to cause it to operate for a predetermined period of time whereby to purify the hot dry air stream. Again, these predetermined periods of time may be preprogrammed in the control circuit whereby the lights can be switched on and off during predetermined cycles.

As shown in FIG. 3 an ion generator 44 may also be disposed in the main distribution channel 17" forwardly of the heater 23 whereby to inject ions in the air stream. The ion generator is also controlled by the control 27 for a desired period of time or cycles of periods of time as desired by the user person whereby to produce an energizing therapeutic effect, as previously described.

Still further, and as illustrated in FIG. 6, an atomizer 45 which consists of a spray nozzle is disposed for communication with the air distribution channel at the juncture of the branch channel 17 or 17' or could communicate directly with the top wall 13 of the therapeutic shower enclosure to produce a fine mist to control a low percentage of humidity in the hot dry air stream. It is also controlled by the control 27 for a predetermined period of time. Temperature sensors as well as other sensors not shown, monitor the air within the enclosure and feed signals to the circuitry of the control 27. The control 27 also controls the blower, the heating element, the generators and the light sources. Accordingly, it can be appreciated that the therapeutic shower enclosure of the present invention incorporates in combination systems providing various therapeutic effects which may be used in combination with the hot dry air therapeutic cleansing and the combination of these are selected by the user person to suit his habits.

The therapeutic shower enclosure of the present invention is a thermal formed enclosure having insulated sidewalls 12 and 12' with thermal insulating material 48 being disposed on the outer surfaces of the sidewalls. As the air streams are injected and flow downwardly against the inner surface of the sidewalls 12 and 12', initially these hot air streams will be cooled by the sidewalls and when returning in the corner area 22 producing a cooling effect in the upper body area of the user person. Such will be produced during the start-up period and last a few minutes while the sidewalls absorb heat to become hot whereby the temperature in the enclosure can stabilize. There is still a certain amount of heat lost through the door assembly 14 which is hereinshown as consisting of glass panels 14' whereby to provide visibility within the enclosure for security reasons. Insulated handles 14" also provide access and displacement of these sliding glass panels 14'. The frame of these panel are preferably polymeric material.

The control panel 27 is herein only schematically illustrated but it preferably consists of push button switches which may actuate programmed control functions which are actuated for predetermined periods of time.

Figure 11:
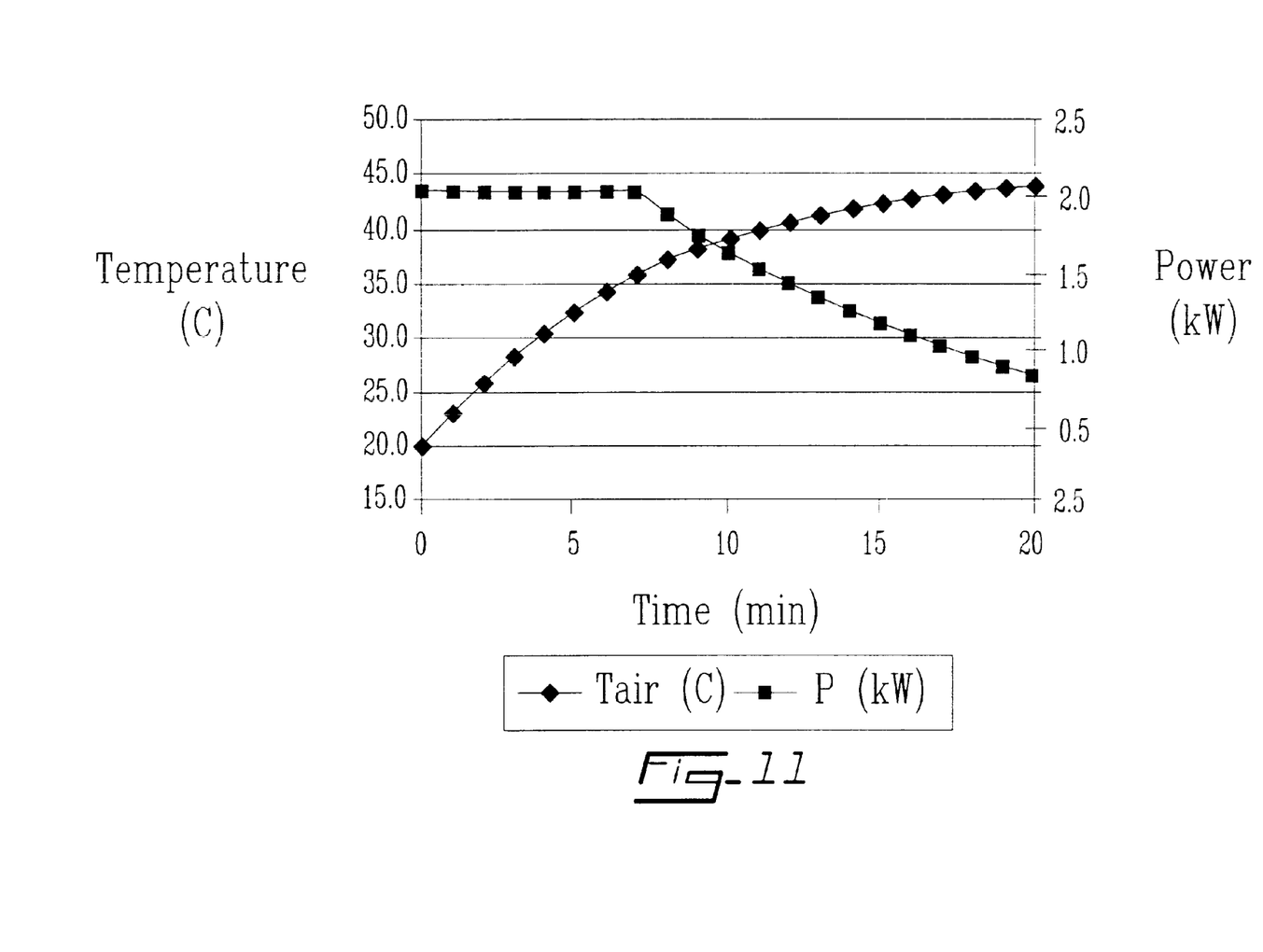
FIG. 11 is a further chart illustrating the variation in temperature and pressure in the therapeutic shower enclosure during a predetermined period of time with a 2 kW fan generating a 100 cfm and the effect of the cooling of the hot air by the sidewalls of the enclosure and its effect on the hot dry air being convected into the enclosure.

FIG. 10 is a chart illustrating various parameters of a hot environment and the areas that a human body can tolerate comfortably up to the intolerable. FIG. 11 is a further chart illustrating the temperature gradient and its rise time in relation to the power of the heater as utilized in a therapeutic shower enclosure constructed in accordance with the present invention.

It is within the ambit of the present invention to cover any obvious modifications of the preferred embodiment described herein provided such modifications fall within the scope of the appended claims.

What is claimed is:

1. A therapeutic shower enclosure comprising a bottom wall, sidewalls, a top wall and a door assembly in said sidewalls for access to said enclosure; an air distribution channel in communication with an air blower and an air return orifice and at least one air injection orifices communicating with said enclosure whereby to create a stream of circulating air in said enclosure, heating means in said air distribution channel for heating air convected therein to a temperature of up to about 50° C. to 75° C. to provide said stream as a stream of hot dry air circulating in said enclosure about a person's body in said enclosure whereby to cause said person's body to increase its internal temperature to cause perspiration to thereby provide a therapeutic effect of shedding toxins through the skin, wherein said sidewalls are disposed at a predetermined angle with respect to each other to define a corner area in said enclosure, said air return orifice being disposed in said top wall in said corner area, therebeing two of said air injecting orifices disposed spaced adjacent said sidewalls on a respective one of said opposed sidewalls forwardly of said corner area whereby to create said stream of hot dry air having a downward path from opposed sides of said enclosure to said bottom wall and then up along said corner area to said air return orifice to subject the user person standing in said enclosure to said dry heat air stream.

2. A therapeutic shower enclosure as claimed in claim 1 wherein said air distribution channel is mounted in said top wall of said enclosure, said air return orifice and at least one air injection orifices being provided in said top wall.

3. A therapeutic shower enclosure as claimed in claim 2 wherein said air blower is mounted in said air distribution channel adjacent a single one of said air return orifice.

4. A therapeutic shower enclosure as claimed in claim 1 wherein said air is heated to a temperature preferably within the range of from about 31° C. to 40° C. and for a predetermined period of time.

5. A therapeutic shower enclosure as claimed in claim 4 wherein said predetermine period of time is about 20 minutes, said temperature being attained within a time delay of about 5 minutes from start-up for said enclosure having a volume of about 62 cubic feet.

6. A therapeutic shower enclosure as claimed in claim 5 wherein said air blower has a displacement capacity of 65 cfm and said air injection orifices are of predetermined sizes, whereby air displacement on a user's skin will not exceed 0.2 m/s.

7. A therapeutic shower enclosure as claimed in claim 1 wherein there are two of said sidewalls disposed at substantially right angles to one another and having a point of juncture in said corner area to define a right angle rear corner of said housing, said air injecting orifices being disposed adjacent a forward end of each said two of said sidewalls.

8. A therapeutic shower enclosure as claimed in claim 7 wherein said air distribution channel is formed in a molded shell which is secured over said top wall of said enclosure, said air distribution channel having an inlet end surrounding at least part of an impeller of said air blower and two branch channels leading to a respective one of said air injecting orifices, said air injecting orifices being elongated slots formed in said top wall spaced close to a respective one of said two sidewalls.

9. A therapeutic shower enclosure as claimed in claim 1 wherein said air injecting orifices are elongated slot orifices dimensioned to provide an accelerated downward air stream adjacent said sidewalls at a pressure sufficient to reach said bottom wall and to create a return air stream comfortable to the head of a user person standing in said enclosure.

10. A therapeutic shower enclosure as claimed in claim 1 wherein said elongated slots each have a dimension of approximately 6 inches by ¾ of an inch, said air return orifice being a circular orifice having a diameter of 3 inches and said air blower having an air displacement capacity of 50 cfm for said enclosure of approximately 36 inches×40 inches×80 inches and wherein said heating means is a 2 kw electric resistive element.

11. A therapeutic shower enclosure as claimed in claim 1 wherein said air return orifice is constituted by a single air return orifice.

12. A therapeutic shower enclosure as claimed in claim 11 wherein there is further provided a shower head and water control valves in said enclosure, and a water deflector cover secured forwardly of said single air return orifices and having collecting throughs for accumulating water droplets at said air return orifice and directing same at said sidewalls.

13. A therapeutic shower enclosure as claimed in claim 11 wherein an air filter support frame is mounted adjacent said air return orifice and supported above said water deflector cover, said frame being adapted to retain an air filter adjacent said air return orifice, said filter being accessible by removal of said water deflector cover.

14. A therapeutic shower enclosure as claimed in claim 13 wherein said water deflector cover is secured to said top wall and said filter support frame by detachable attachment means.

15. A therapeutic shower enclosure as claimed in claim 14 wherein said detachable attachment means are Velcro™ attachment patches.

16. A therapeutic shower enclosure as claimed in claim 1 wherein there is further provided in combination with said hot dry air therapeutic stream a chromotherapeutic light source to subject a user person to colored light, a luminotherapeutic light source to subject a user person to intense light, an ion generating source to inject ions in said air stream and an ozone generator to inject ozone in said air stream.

17. A therapeutic shower enclosure as claimed in claim 16 wherein there is further provided control means having several programmed control functions, and push button switches and symbols associated with said switches for switching "on" or "off" said programmed functions.

18. A therapeutic shower enclosure as claimed in claim 1 wherein there is further provided at least one colored light source mounted in said top wall, and control means to energize said light source for a desired predetermined period of time to subject a user person to a chromotherapeutic effect.

19. A therapeutic shower enclosure as claimed in claim 18 wherein there are three of said colored light source, each said source comprising a plurality of red, blue and green light emitting diodes, said light sources being disposed at a position variable to a user person's head standing in said shower enclosure.

20. A therapeutic shower enclosure as claimed in claim 18 wherein said light source comprises a plurality of light emitting diodes, there being three or more groups of different colored diodes, said groups of diodes being actuated to produce a desired resultant colored light source.

21. A therapeutic shower enclosure as claimed in claim 20 wherein said groups of colored diodes are connected to light intensity control means to modulate the light intensity thereof to provide a color mix to generate said desired resultant colored light source.

22. A therapeutic shower enclosure as claimed in claim 1 wherein there is further provided at least one intense clear light source in said top wall, and control means to actuate said intense clear light source for a desired predetermined period of time to subject a user person to a luminotherapeutic effect.

23. A therapeutic shower enclosure as claimed in claim 22 wherein said intense light source is one of halogen light source, a neon light source or the like light sources.

24. A therapeutic shower enclosure as claimed in claim 23 wherein there are two or more halogen light sources secured in said top wall.

25. A therapeutic shower enclosure as claimed in claim 1 wherein there is further provided an ion generator in communication with said air distribution channel to inject ions in said hot dry air stream, and control means to actuate said ion generator for a desired predetermined period of time to subject a user person to an energizing therapeutic effect.

26. A therapeutic shower enclosure as claimed in claim 25 wherein said ion generator is secured to said air distribution channel between said air blower and said heating means.

27. A therapeutic shower enclosure as claimed in claim 1 wherein there is further provided an ozone generator in communication with said air distribution channel to inject ozone in said hot dry air stream, and control means to actuate said ozone generator for a desired predetermined period of time to subject a user person to a purified hot dry air stream.

28. A therapeutic shower enclosure as claimed in claim 1 wherein there is further provided a water atomizer spray nozzle in communication with the interior of said enclosure to inject a fine water mist herein, and control means to control the operation of said water atomizer for a predetermined period of time.

29. A therapeutic shower enclosure as claimed in claim 1 wherein said air return orifice is a single air return orifice of circular contour, and an air deflector disc secured to said top wall and aligned concentrically with said air return orifice and spaced a predetermined distance forwardly thereof.

30. A therapeutic shower enclosure as claimed in claim 1 wherein there is further provided control means to control the operation of said air blower for a predetermined period of time within a time span of from about 5 to 30 minutes.

31. A therapeutic shower enclosure as claimed in claim 30 wherein said shower enclosure is a thermo-formed enclosure having insulated sidewalls.

32. A therapeutic shower enclosure as claimed in claim 31 wherein said door assembly comprises a plurality of glass panels retained between a top guide track and bottom rail, some of said panels being slidingly displaced on said bottom rail.

33. A therapeutic shower enclosure comprising a bottom wall, sidewalls, a top wall and a door assembly in said sidewalls for access to said enclosure, one or more chromotherapeutic light source secured to one of said top wall or sidewalls of said enclosure to subject a user person to colored light, and control means to energize said light source for a desired predetermined period of time to subject a user person to a chromotherapeutic effect, wherein there is further provided an air distribution channel in communication with an air blower and an air return orifice and at least one air injection orifices communicating with said enclosure whereby to create a stream of circulating air in said enclosure, heating means in said air distribution channel for heating air convected therein to a temperature of up to about 50° C. to 75° C. to provide said stream as a stream of hot dry air circulating in said enclosure about a person's body in said enclosure whereby to cause said person's body to increase is internal temperature to cause perspiration to thereby provide a therapeutic effect of shedding toxins through the skin, wherein said sidewalls are disposed at a predetermined angle with respect to each other to define a corner area in said enclosure, said air return orifice being disposed in said top wall in said corner area, therebeing two of said air injecting orifices disposed spaced adjacent said sidewalls on a respective one of said opposed sidewalls forwardly of said corner area whereby to create said stream of hot dry air having a downward path from opposed sides of said enclosure to said bottom wall and then up along said corner area to said air return orifice to subject the user person standing in said enclosure to said dry heat air stream.

34. A therapeutic shower enclosure as claimed in claim 33 wherein said one or more chromotherapeutic light source is secured to said top wall of said enclosure at a position to direct said colored light for visibility by a user person.

35. A therapeutic shower enclosure as claimed in claim 34 wherein said light source comprises a plurality of light emitting diodes, there being three or more groups of different colored diodes, said groups of diodes being actuated to produce a desired resultant colored light source.

36. A therapeutic shower enclosure as claimed in claim 35 wherein said groups of colored diodes are connected to light intensity control means to vary the light intensity thereof to provide a color mix to generate said desired resultant colored light source.

37. A therapeutic shower enclosure as claimed in claim 33 wherein there is further provided a shower head and water control valves in said enclosure, and a water deflector cover secured forwardly of said single air return orifices and having collecting throughs for accumulating water droplets at said air return orifice and directing same at said sidewalls.

38. A therapeutic shower enclosure as claimed in claim 37 wherein an air filter support frame is mounted adjacent said air return orifice and supported above said water deflector cover, said frame being adapted to retain an air filter adjacent said air return orifice, said filter being accessible by removal of said water deflector cover.

39. A therapeutic shower enclosure as claimed in claim 34 wherein said air distribution channel is mounted in said top wall of said enclosure, said air return orifice and at least one air injection orifices being provided in said top wall.

40. A therapeutic shower enclosure comprising a bottom wall, sidewalls, a top wall and a door assembly in said sidewalls for access to said enclosure, one or more intense clear light source in one of said top wall or sidewalls having an intensity of at least 2000 lux, control means to energize said light source for a desired predetermined period of time to subject a user person to a luminotherapeutic effect, said enclosure having a shower head and water control valves, wherein there is further provided an air distribution channel in communication with an air blower and an air return orifice and at least one air injection orifices communicating with said enclosure whereby to create a stream of circulating air in said enclosure, heating means in said air distribution channel for heating air convected therein to a temperature of up to about 50° C. to 75° C. to provide said stream as a stream of hot dry air circulating in said enclosure about a person's body in said enclosure whereby to cause said person's body to increase is internal temperature to cause perspiration to thereby provide a therapeutic effect of shedding toxins through the skin, wherein said sidewalls are disposed at a predetermined angle with respect to each other to define a corner area in said enclosure, said air return orifice being disposed in said top wall in said corner area, therebeing two of said air injecting orifices disposed spaced adjacent said sidewalls on a respective one of said opposed sidewalls forwardly of said corner area whereby to create said stream of hot dry air having a downward path from opposed sides of said enclosure to said bottom wall and then up along said corner area to said air return orifice to subject the user person standing in said enclosure to said dry heat air stream.

\* \* \* \* \*